United States Patent [19]

Montalvo

[11] Patent Number: 5,476,460
[45] Date of Patent: Dec. 19, 1995

[54] IMPLANTABLE INFUSION PORT WITH REDUCED INTERNAL VOLUME

[75] Inventor: Rudolph A. Montalvo, Woodland Hills, Calif.

[73] Assignee: Minimed Inc., Sylmar, Calif.

[21] Appl. No.: 235,463

[22] Filed: Apr. 29, 1994

[51] Int. Cl.⁶ .................................................. A61M 5/14
[52] U.S. Cl. ......................... 604/891.1; 604/93; 604/8; 128/DIG. 12
[58] Field of Search ............................... 604/891.1, 93, 604/131, 244, 175, 48, 8–9, 115–117, 132–134, 183–185; 128/DIG. 12; 4/415

[56] References Cited

U.S. PATENT DOCUMENTS

| | | |
|---|---|---|
| 3,910,298 | 10/1975 | Shotmeyer . |
| 4,464,178 | 8/1984 | Dalton . |
| 4,790,826 | 12/1988 | Elftman . |
| 5,147,483 | 9/1992 | Melsky et al. . |
| 5,207,644 | 5/1993 | Strecker . |
| 5,218,725 | 6/1993 | Lipman . |
| 5,249,314 | 10/1993 | Sweeny et al. . |
| 5,259,075 | 11/1993 | Cutler . |
| 5,387,192 | 2/1995 | Glantz et al. . |

FOREIGN PATENT DOCUMENTS

| | | |
|---|---|---|
| 2037360 | 8/1992 | Canada . |
| 2683562 | 5/1993 | France . |

*Primary Examiner*—C. Fred Rosenbaum
*Assistant Examiner*—Perry E. Van Over
*Attorney, Agent, or Firm*—Kelly, Bauersfeld & Lowry

[57] ABSTRACT

An implantable infusion port is provided to facilitate delivery of medication to a patient, wherein the infusion port has a substantially reduced internal volume to minimize the quantity of residual medication therein. The infusion port comprises a cup-shaped housing with a self-sealing septum mounted thereon to define an internal chamber for receiving medication infused through the patient's skin and the septum via a hypodermic needle or the like. A catheter mounted on the housing communicates with the internal chamber to deliver the medication to a selected site within the patient. A substantial portion of the chamber volume is occupied by inert beads which minimize the open volume of the chamber and thereby maximize medication delivery to the patient.

19 Claims, 2 Drawing Sheets

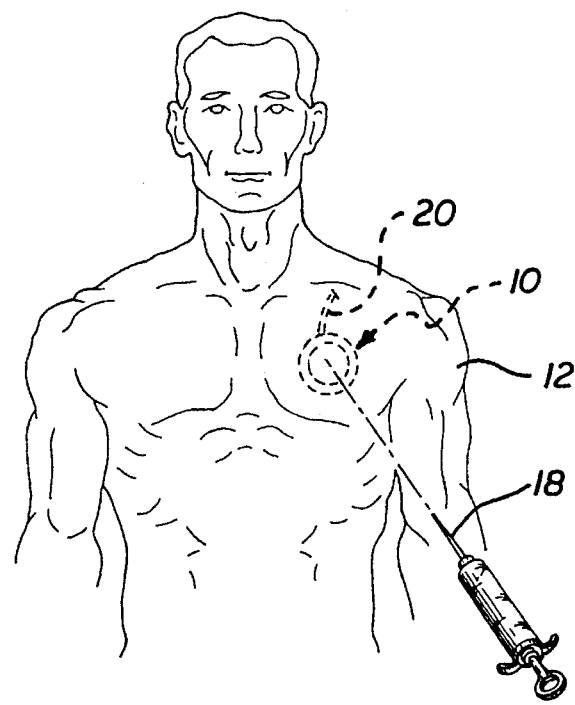
FIG. 1
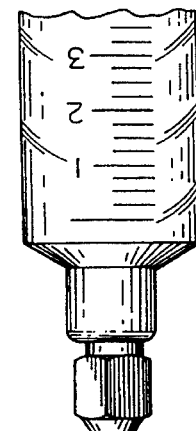
FIG. 2
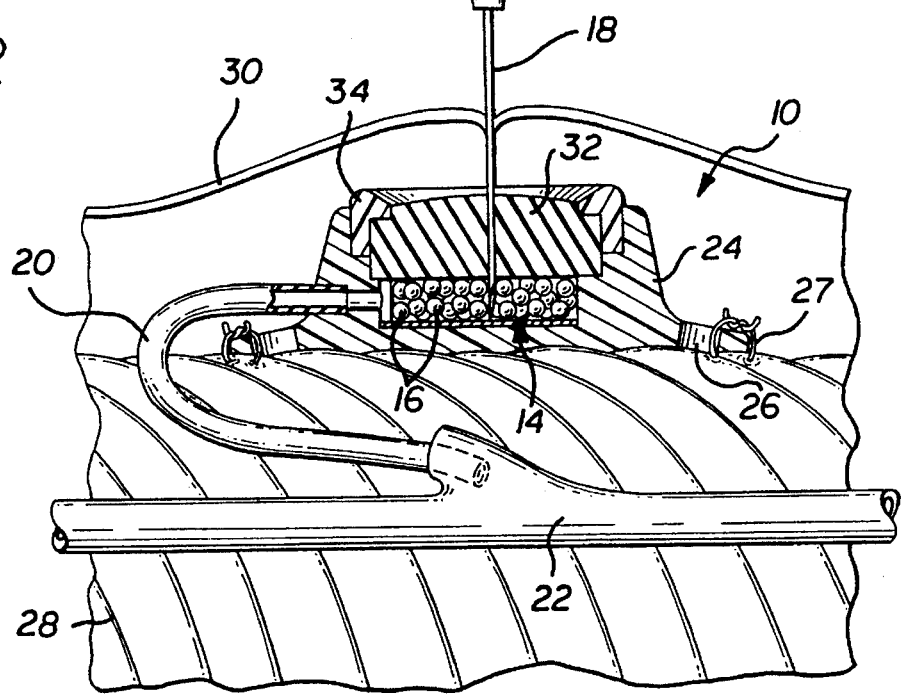

5,476,460

IMPLANTABLE INFUSION PORT WITH REDUCED INTERNAL VOLUME

BACKGROUND OF THE INVENTION

This invention relates generally to implantable infusion ports of type utilized for frequent administration of medication to a patient. More particularly, this invention relates to an improved infusion port designed with a reduced or minimal internal volume to provide substantially maximum delivery of medication to the patient, with minimal residual medication remaining within the infusion port.

Implantable infusion ports are generally known in the art to include a relatively compact and generally cup-shaped housing having a resilient self-sealing septum mounted over the open end thereof to define a medication receiving chamber. The housing and septum are surgically implanted into the body of a patient at a position closely underlying the skin and subcutaneous tissue, and with the septum presented toward the patient's skin. The infusion port is adapted for palpable identification through the skin to receive medication in liquid form injected via a hypodermic needle or cannula through the skin and septum into the medication chamber. A catheter mounted on the housing communicates with the medication chamber to deliver the medication to a selected site within the patient. In this regard, the catheter is often placed for delivering the medication to the patient's vascular system, whereby such implantable infusion ports are sometimes referred to as vascular access devices.

Implantable infusion ports of this general type are typically used to facilitate injection or infusion of medication in liquid form on a frequent basis. More specifically, the implanted port can be accessed transcutaneously with a hypodermic needle or the like on a frequent and repeated basis, and over an extended period of time, with minimal patient discomfort. The infusion port provides accurate delivery of medication to a specific delivery site within the patient, without complications associated with repeated intravenous puncture or the infection risk associated with a transcutaneous catheter. One common application for an implantable infusion port is the administration of chemotherapy agents. Delivery of other medications such as insulin, pain medication, etc., on a frequent basis has also been proposed.

To insure accurate delivery of the selected medication to the internal chamber of an implanted infusion port, the self-sealing septum has been designed with a substantial surface area for accurate palpable identification through the skin of the patient. In addition, to ensure fully seated reception of the typically chisel-tipped injection needle, the medication chamber has been designed with a substantial depth dimension. Unfortunately, these design factors inherently require the medication chamber of the infusion port to have a substantial internal volume, especially in comparison with relatively small volume doses of medication to be administered to the patient. As a result, when medication is injected into the chamber, a potentially significant quantity of the medication is required to fill the volume of the chamber before any medication is in fact delivered to the patient. Moreover, at the conclusion of an injection step, a significant quantity of the medication will remain as a residue within the internal chamber of the infusion port. Although such residue medication may be dislodged and delivered to the patient at a later time in the course of a subsequent injection step, degradation can occur quickly with some medicaments such that the effectiveness is reduced or lost. While it is often possible to compensate for the degraded and ineffective medication residue by simply increasing the dose injected into the infusion port chamber, the relatively high cost of many medications makes increased dosages undesirable.

There exists, therefore, a significant need for improvements in implantable infusion ports, particularly with respect to maximizing the quantity of injected medication which is actually and immediately administered to the patient, while concurrently minimizing the presence of residual medication in the infusion port. The present invention fulfills these needs and provides further related advantages.

SUMMARY OF THE INVENTION

In accordance with the invention, an improved implantable infusion port is provided for facilitating administration of medication to a patient. The infusion port is adapted for subcutaneous implantation into the patient's body and defines a medication receiving chamber into which medication can be injected or infused transcutaneously. The medication chamber has a substantial portion of its total volume occupied by inert beads, thereby minimizing the available open volume of the chamber for receiving the injected medication. As a result, a substantially maximized proportion of the injected medication is actually delivered to the patient, with a correspondingly minimized quantity of residual medication remaining within the medication chamber.

The implantable infusion port comprises a generally cup-shaped housing having a self-sealing resilient septum mounted over the open end thereof and cooperating therewith to define the medication receiving chamber. The housing and septum are sized and shaped for subcutaneous implantation in a position with the septum presented toward the patient's skin, and for palpable identification through the skin. A catheter is carried by the housing and communicates with the medication chamber for passage of medication to a selected site within the patient. Medication is delivered to the medication chamber via a hypodermic needle or cannula or the like passed through the skin and the septum. The surface area of the septum together with the depth of the medication chamber are designed for easy and accurate injection of the medication into the chamber.

In accordance with the invention, the inert beads are provided in the form of a relatively large plurality of spheres which occupy a substantial portion of the total internal volume of the medication chamber. In the preferred form, these beads have a relatively hard yet nonbrittle, nonporous, and lightweight construction resistant to deformation or damage upon insertion of a hypodermic needle or the like through the septum into the medication chamber. Instead, the beads slide over one another relatively freely to facilitate and permit substantially unobstructed needle insertion for medication delivery into the medication chamber. The sizes of the beads are selected to avoid obstructing or occluding the catheter, and one or more internal ribs may be formed on the housing at an inlet end of the catheter to prevent catheter occlusion by the beads. While the volume occupied by the beads may vary, a bead volume on the order of at least 50% and desirably about 80% of the total chamber volume is preferred. When medication is injected into the chamber, a substantial proportion thus passes directly to the catheter for immediate administration to the patient, with minimal residual medication remaining within the relatively small open volume of the chamber.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a diagrammatic view illustrating an infusion port implanted within the body of a patient;

FIG. 2 is an enlarged fragmented sectional view illustrating the subcutaneously implanted infusion port of FIG. 1;

DETAILED DESCRIPTION OF THE PREFERRED EMBODIMENT

Figure 3:
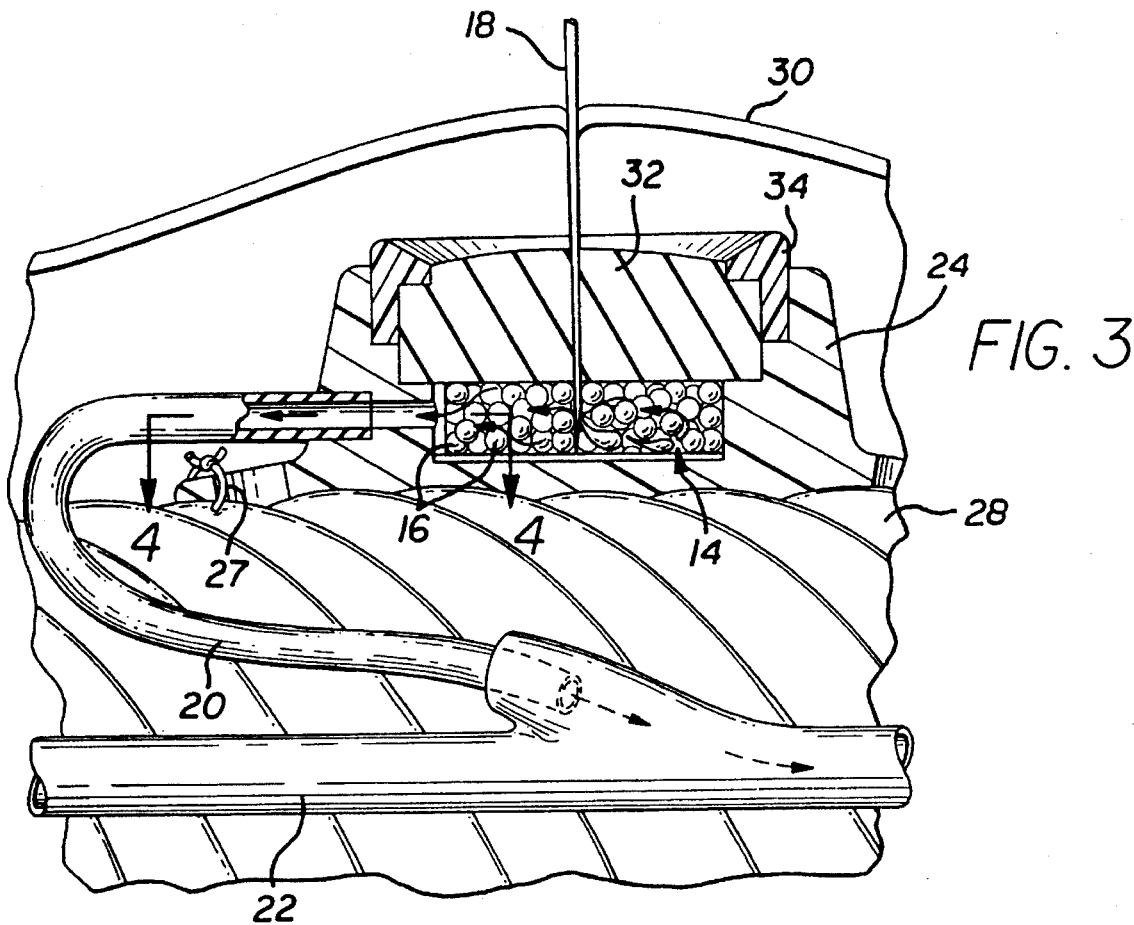
FIG. 3 is an enlarged fragmented vertical sectional view similar to FIG. 2 and depicting medication administration through the infusion port to the patient.
Figure 4:
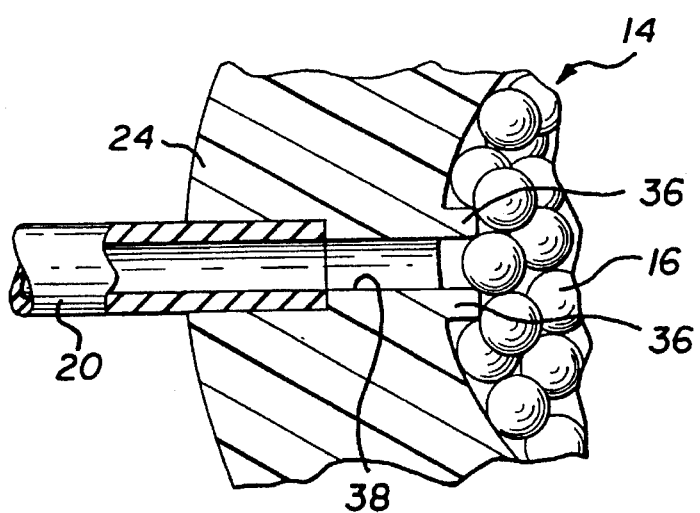
FIG. 4 is an enlarged sectional view taken generally on the line 4—4 of FIG. 3.

As shown in the exemplary drawings, an improved implantable infusion port referred to generally in FIG. 1 by the reference numeral 10 is provided for subcutaneous implantation into the body of a patient 12. As shown in FIGS. 2–4, the implantable infusion port 10 defines an internal chamber 14 for receiving medication administered to a patient, wherein a substantial portion of the total internal volume of the chamber 14 is occupied by a plurality of beads 16. The beads 16 thus substantially reduce the available open volume of the medication chamber 14, such that residual medication within the chamber is substantially minimized.

The infusion port 10 shown in FIGS. 1–4 has a generally conventional overall construction for use in facilitated administration of medication in liquid form to a patient. In this regard, the infusion port 10 comprises a relatively compact device which is normally adapted for subcutaneous implantation into the body of a patient 12 at a selected and convenient position proximal to a selected medication delivery site. The infusion port is designed for transcutaneous access by means of a hypodermic needle 18 or cannula or the like for delivering the medication to the internal chamber 14, typically on a relatively frequent basis. The administered medication passes through the internal chamber 14 and further through a catheter 20 or the like for delivery to the patient. In this regard, as depicted in FIGS. 2 and 3, the distal end of the catheter 20 is often positioned to deliver the medication to the patient's vascular system such as to a vein 22, whereby implantable infusion ports of this general type are sometimes referred to as vascular access devices.

The infusion port comprises a generally cup-shaped housing 24 having an enlarged outer rim 26 adapted for attachment by sutures 27 or the like to the muscle fascia 28 (FIGS. 2 and 3) beneath the patient's skin 30. The housing 24 may be constructed from a relatively hard plastic material or metal components, as desired, to define the medication chamber 14 which opens in an outward direction toward the skin 30. A resilient self-sealing septum 32 of a selected elastomer or other suitable material is mounted by a cap ring 34 or the like securely onto the housing 24 to close the outboard side of the chamber 14. The catheter 20 is mounted on the housing with a proximal or inlet end communicating with the interior of the chamber 14 for flow of medication therefrom to the patient.

The overall size and shape of the infusion port 10 and its implanted location within the patient 12 are chosen for relatively simple and accurate palpable identification through the skin 30. With this construction, the septum 32 can be accurately located with the distal end of the hypodermic needle 18 or the like passed through the patient's skin 30. Accordingly, when medication delivery to the patient is desired, the hypodermic needle 18 can be passed transcutaneously through the skin 30 and the septum 32 for delivering the selected medication into the chamber 14, and for flow therefrom through the catheter 20 to the patient.

In accordance with the primary aspect of the invention, the plurality of beads 16 are disposed within the medication chamber 14 and occupy a substantial portion of the total volume thereof. As a result, the chamber 14 presents a relatively minimal open internal volume for receiving the medication, while providing a substantial total volume in terms of breadth and depth for relatively easy and accurate registration with the needle 18. Medication injected into the chamber 14 thus flows to the catheter 20 for administration to the patient with minimal residence within the chamber 14, and with minimal residue remaining within the chamber at the conclusion of an injection step.

The beads 16 have a size and shape to accommodate insertion of the needle 18 substantially without interference or damage to the beads or to the needle. In this regard, the preferred beads 16 have a relatively hard and nonbrittle construction resistant to chipping or deformation upon needle contact. The beads are preferably provided with a spherical construction to move over one another relatively easily with a sliding action, and thereby permit substantially unobstructed needle insertion into the chamber 14 without damage to the chiseled tip of the needle. In addition, the beads 16 are substantially inert with respect to the injected medication, and desirably have a lightweight construction which is generally smooth and nonporous to avoid or minimize absorption and/or adsorption of the medication. Although a variety of relatively hard and chemically inert bead materials may be used, preferred materials include polyolefin plastics such as polypropylene. Alternately, beads formed from or coated with Teflon may also be used for enhancing sliding action upon needle insertion.

The size of the beads 16 is selected to occupy a substantial proportion of the total chamber volume yet avoid undesired occlusion of the catheter 20. In this regard, the preferred bead sizes are selected to be substantially greater than the internal diameter of the catheter 20. For example, for use with a catheter bore size of about 0.040 inch, a bead diameter of about 0.060 inch is contemplated, with a total number of beads to occupy at least about fifty percent and desirably about eighty percent of the total chamber volume. In addition, in the preferred form, a small spacer rib or ribs 36 (FIG. 4) may be formed within the cup-shaped housing 24 at a position adjacent an exit port 38 connected to the catheter inlet end to maintain the beads in spaced nonoccluding relation with the catheter.

The improved implantable infusion port of the present invention thus substantially reduces the open internal volume of the medication receiving chamber 14, substantially without reducing the overall size and shape of the infusion port. As a result, the chamber 14 can be palpably located quickly and easily for facilitated injection of medication through the septum 32 and into the chamber 14. Due to the small open volume of the chamber, the majority of the injected medication flows immediately to and through the catheter 20 for delivery to the patient. Moreover, medication residue remaining in the chamber at the conclusion of an injection step is substantially minimized.

A variety of modifications and improvements to the invention will be apparent to those skilled in the art. Accordingly, no limitation on the invention is intended by way of the foregoing description and accompanying drawings, except as set forth in the appended claims.

What is claimed is:

1. An implantable infusion port for subcutaneous implantation into the body of a patient, comprising:
   a generally cup-shaped housing having an open end;
   a self-sealing septum mounted on said housing over the open end thereof and cooperating therewith to define a medication chamber;
   catheter means connected to said housing for delivering medication from said chamber to a patient; and
   a plurality of substantially inert beads disposed within said chamber and occupying a substantial portion of the total chamber volume.

2. The implantable infusion port of claim 1 wherein said beads are formed from a relatively hard and nonbrittle material.

3. The implantable infusion port of claim 2 wherein said beads are formed from a lightweight plastic material.

4. The implantable infusion port of claim 3 wherein said beads are formed from a polyolefin material.

5. The implantable infusion port of claim 4 wherein said beads are formed from polypropylene.

6. The implantable infusion port of claim 1 wherein said beads are spheres.

7. The implantable infusion port of claim 1 wherein said beads are substantially nonporous.

8. The implantable infusion port of claim 1 wherein said housing defines an exit port, said catheter means being connected to said housing in communication with said exit port, said housing further including at least one spacer rib for preventing said beads from occluding said exit port.

9. The implantable infusion port of claim 1 wherein said beads occupy at least about fifty percent of the total volume of said chamber.

10. The implantable infusion port of claim 9 wherein said beads occupy about eighty percent of the total volume of said chamber.

11. In an infusion device for delivering a medication to a patient, said infusion device having a housing defining a chamber for receiving the medication, and an exit port formed in said housing for flow of the medication from said chamber to the patient, the improvement comprising a plurality of beads disposed within said chamber to occupy a substantial portion of the total chamber volume.

12. The infusion device of claim 11, wherein said housing includes:
   a generally cup-shaped housing member having an open end, a self-sealing septum mounted on said housing member over the open end thereof and cooperating therewith to define a medication chamber, and;
   catheter means connected to said housing member for delivering medication from said chamber to a patient.

13. The infusion device of claim 11 wherein said beads are formed from a substantially inert material.

14. The infusion device of claim 13 wherein said beads are formed from a polyolefin material.

15. The infusion device of claim 13 wherein said beads are formed from polypropylene.

16. The infusion device of claim 11 wherein said beads occupy at least about fifty percent of the total volume of said chamber.

17. The infusion device of claim 11 wherein said beads occupy about eighty percent of the total volume of said chamber.

18. The infusion device of claim 11 wherein said housing member has said has exit port formed therein and further includes rib means for preventing occlusion of said exit port by said beads.

19. The infusion device of claim 11 wherein said beads are formed from a substantially nonporous material.

* * * * *